United States Patent [19]

Ryckaert et al.

[11] 4,392,000

[45] Jul. 5, 1983

[54] STABILIZED COMPOSITIONS OF CHLORINATED SOLVENTS

[75] Inventors: Andre' Ryckaert, Brussels; Michel Servais, Kraainem, both of Belgium

[73] Assignee: Solvay & Cie., Brussels, Belgium

[21] Appl. No.: 312,814

[22] Filed: Oct. 19, 1981

[30] Foreign Application Priority Data

Oct. 23, 1980 [FR] France .................... 80 22749

[51] Int. Cl.$^3$ .................. C07C 17/42; C11D 7/50; C23G 5/02
[52] U.S. Cl. .................. 570/104; 106/311; 252/171; 252/364; 252/406; 570/102; 570/109; 570/111; 570/114
[58] Field of Search ............... 252/364, 170, 171, 406; 106/311; 570/102, 104, 109, 111, 114

[56] References Cited

U.S. PATENT DOCUMENTS

| | | | |
|---|---|---|---|
| 3,496,241 | 2/1970 | Berkowitz | 252/364 |
| 3,546,125 | 12/1970 | Archer et al. | 252/364 |
| 3,546,305 | 12/1970 | Archer et al. | 252/364 |
| 3,549,547 | 12/1970 | McDonald et al. | 252/364 |
| 3,565,811 | 2/1971 | McDonald et al. | 252/364 |
| 3,629,128 | 12/1971 | Rains | 252/364 |
| 3,641,169 | 2/1972 | Crabb et al. | 252/364 |
| 3,878,256 | 4/1975 | Richzenhain et al. | 252/364 |
| 3,959,397 | 5/1976 | Richzenhain et al. | 252/364 |
| 4,046,820 | 9/1977 | Goodner et al. | 252/364 |
| 4,057,973 | 11/1977 | Murphy et al. | 252/364 |

FOREIGN PATENT DOCUMENTS

| | | |
|---|---|---|
| 638938 | 11/1963 | Belgium. |
| 2108015 | 5/1972 | France. |
| 912118 | 12/1962 | United Kingdom. |
| 1315884 | 5/1973 | United Kingdom. |

OTHER PUBLICATIONS

Heterocyclic Compounds with Three-and Four-Membered Rings", Editor Weissberger, Part One, Interscience, 1964, Chapter 4.

*Primary Examiner*—Irwin Gluck
*Attorney, Agent, or Firm*—Spencer & Kaye

[57] ABSTRACT

The invention relates to compositions of chlorinated solvents such as 1,1,1-trichloroethane, stabilized by means of a heterocyclic compound containing oxaziridine units, such as 2-tert.-butyloxaziridine.

17 Claims, No Drawings

STABILIZED COMPOSITIONS OF CHLORINATED SOLVENTS

BACKGROUND OF THE INVENTION

The present invention relates to stabilised compositions of chlorinated solvents such as methylene chloride, trichloroethylene, perchloroethylene and 1,1,1-trichloroethane.

It is possible to obtain stable compositions of chlorinated solvents such as methylene chloride, trichloroethylene, perchloroethylene and 1,1,1-trichloroethane, which compositions can be used, in particular, for the degreasing of metals, for the dry-cleaning of textiles and in aerosols, by adding, to the chlorinated solvent, chemical products referred to as stabilisers, which can be chosen from amongst a multitude of chemical compounds of varied types. Depending on the chlorinated solvent in question and the application for which it is intended, different stabilisers are chosen and they are used in different amounts. The best stabilisation formulations are still selected by largely empirical methods. However, it is observed that there is currently a general tendency, for all chlorinated solvents, to resort to very complex stabilisation formulations containing a large number of different stabilisers, the latter being used in these formulations in large proportions.

SUMMARY OF THE INVENTION

The aim of the present invention is to provide, for the stabilisation of chlorinated solvents, new, particularly effective stabilisers which make it possible to simplify the stabilisation formulations and to reduce the amounts of stabiliser to be used.

For this purpose, the invention relates to compositions of chlorinated solvents, stabilised by means of a heterocyclic compound containing an oxaziridine ring.

The expression "heterocyclic compound containing an oxaziridine ring" is understood to denote any chemical compound containing at least one ring of the formula

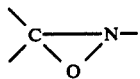

DETAILED DESCRIPTION OF THE INVENTION

In general, a heterocyclic compound of the general formula

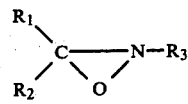

is used, in which $R_1$, $R_2$ and $R_3$ are different or identical organic or inorganic radicals. Preferably, $R_1$, $R_2$ and $R_3$ independently of one another represent a hydrogen atom, saturated or unsaturated, aliphatic or cycloaliphatic radicals optionally substituted by other groups or atoms, or aromatic radicals. Most frequently, $R_1$, $R_2$ and $R_3$ are chosen from amongst the hydrogen atom, alkyl radicals containing from 1 to 8 carbon atoms and aromatic radicals containing not more than 8 carbon atoms. Preferably, $R_1$, $R_2$ and $R_3$ are the hydrogen or saturated alkyl radicals containing from 1 to 5 carbon atoms. The very particularly preferred compounds are those in which at least one of the radicals $R_1$, $R_2$ or $R_3$ is a branched alkyl radical. Finally, amongst these, the preferred compounds are those in which at least the radical $R_3$ is a branched alkyl radical. Examples of suitable compounds which may be mentioned are 2-tert.-butyloxaziridine, 2-tert.-amyloxaziridine, 2-isopropyloxaziridine, 3-methyl-2-tert.-butyloxaziridine, 3-methyl-2-tert.-amyloxaziridine, 3-methyl-2-isopropyloxaziridine, 3,3-dimethyl-2-tert.-butyloxaziridine, 3,3-dimethyl-2-tert.-amyloxaziridine, 3,3-dimethyl-2-isopropyloxaziridine, 3-methyl-3-ethyl-2-tert.-butyloxaziridine, 3-methyl-3-ethyl-2-tert.-amyloxaziridine, 3-methyl-3-ethyl-2-isopropyloxaziridine, 3-ethyl-2-tert.-butyloxaziridine, 3-ethyl-2-tert.-amyloxaziridine, 3-ethyl-2-isopropyloxaziridine, 3-propyl-2-isopropyloxaziridine and 3-isopropyl-2-isopropyloxaziridine. Amongst these, 2-tert.-butyloxaziridine, 2-tert.-amyloxaziridine and 2-isopropyloxaziridine are the most suitable.

2-Tert.-butyloxaziridine is very particularly preferred.

The heterocyclic compounds of the invention, containing the oxaziridine ring, can be prepared by any process known for this purpose, in particular by the processes described in "Heterocyclic compounds with three or four membered rings", Part One-Chapter IV, Editor Arnold Weissberger, 1964, Interscience Publ. Wiley & Sons Inc.-New York-London-Sydney, pages 624 to 646.

The amount of heterocyclic compound to be used varies according to the nature of the chlorinated solvent, according to the nature of the co-stabilisers used and according to the application for which the chlorinated solvent is intended. Usually, this amount varies between 0.0001 and 1 mol per liter of chlorinated solvent. The preferred amounts are between 0.001 and 0.5 mol/liter and very particularly preferred amounts are between 0.01 and 0.2 mol/liter.

The chlorinated solvents which can be stabilised according to the invention can be of very diverse types. In general, they are aliphatic or aromatic compounds containing from 1 to 6 carbon atoms and at least one chlorine atom. The most customary chlorinated solvents are chlorine derivatives of methane, of ethane or of ethylene, such as methylene chloride, chloroform, 1,2-dichloroethane, trichloroethylene, perchloroethylene and 1,1,1-trichloroethane. The invention proves to be particularly advantageous in the case of 1,1,1-trichloroethane, which is reputed to be the most unstable of these chlorinated solvents and which is used on a large scale, hot, cold or in the vapour phase, for the degreasing of metals.

Apart from the abovementioned heterocyclic compounds, the stabilised compositions of chlorinated solvents, according to the invention, can contain other co-stabilisers suitable for the stabilisation of the chlorinated solvents in question. Amongst the most frequently used co-stabilisers, there may be mentioned epoxidised compounds, alcohols, nitroalkanes, esters, nitriles, internal ethers, ketones, amines, phenols and olefinic compounds.

The epoxidised compounds which can be used as co-stabilisers can be saturated or unsaturated. Usually, they are epoxidised compounds of the saturated type, containing up to seven carbon atoms, such as epoxypropane, epoxybutane, 2-methylepoxypropane, 2-methylepoxybutanes and epichlorohydrin.

The alcohols which can be used as co-stabilisers can be saturated or unsaturated. The preferred alcohols contain from 1 to 7 carbon atoms and can be substituted or unsubstituted. Generally, they are unsubstituted alcohols. Examples of saturated alcohols are methanol, ethanol, propanol, isopropanol, butan-1-ol, butan-2-ol, tertiary butyl alcohol, pentanols such as tertiary amyl alcohol, methylcellosolve, ethylcellosolve, propylcellosolve, butylcellosolve, glycerol, ethylene glycol, propylene glycol, 2-hydroxy-2-methylbutan-3-one, 3,3-dimethoxy-2-methylbutan-2-ol and 3-amino-2-methylbutan-2-ol. Excellent results have been obtained with propanols, tertiary and secondary butanols and tertiary pentanol. The preferred saturated alcohol is tertiary butanol. The unsaturated alcohols which are normally used are unsubstituted alcohols containing from 3 to 6 carbon atoms. Amongst these, allyl alcohol, 2-methyl-but-3-en-2-ol and 2-methyl-but-3-yn-2-ol are preferred.

The most preferred unsaturated alcohol is 2-methylbut-3-yn-2-ol.

The nitroalkanes which can be used as co-stabilisers usually contain from 1 to 4 carbon atoms. Preferably, nitromethane, nitroethane, 1- or 2-nitropropane or mixtures of these compounds are used. Nitromethane and nitroethane are very particularly preferred.

The esters which can be used as co-stabilisers are most frequently saturated or unsaturated monoesters and diesters containing from 2 to 8 carbon atoms, which can be substituted by halogens or hydroxyl groups, such as ethyl, propyl, isopropyl, butyl, sec.-butyl, tert.-butyl, amyl, hexyl and cyclohexyl formates, methyl, ethyl, propyl, isopropyl, butyl, amyl, ethynyl or propynyl acetates, methyl, ethyl, propyl, isopropyl, butyl, amyl and ethynyl propionates, methyl, ethyl, propyl, isopropyl and prop-2-ynyl butyrates, methyl, ethyl, propyl, isopropyl, butyl, sec.-butyl and tert.-butyl acrylates and methacrylates, methyl and ethyl crotonates and isocrotonates, ethyl and methyl sorbates, ethyl diformate and ethyl diacetate. Unsubstituted monoesters containing from 4 to 6 carbon atoms are suitable. Excellent results have been obtained with ethyl acetate, isobutyl acetate, n-propyl acetate, methyl methacrylate and n-butyl acetate. Methyl methacrylate, ethyl acetate and n-propyl acetate have proved to be particularly suitable.

The nitriles which can be used as co-stabilisers are most frequently optionally substituted, saturated or unsaturated, aliphatic or aromatic compounds containing from 2 to 7 carbon atoms, such as acetonitrile, propionitrile, acrylonitrile, butyronitrile, methacrylonitrile, malononitrile, benzonitrile, dimethylaminoacetonitrile, methylaminopropionitrile, dimethylaminopropionitrile, diethylaminoacetonitrile, methylethylaminoacetonitrile, thiodipropionitrile, tetracyanoethylene, tetracyanoquinodimethane, tetracyanodithiine, 1,2-dicyano-1,2-bis-(trifluoromethyl)-ethylene, cyanobenzaldehyde, nitrobenzonitrile and cyanopyridine. Amongst these, acetonitrile, propionitrile and acrylonitrile are the most suitable.

The internal ethers which are particularly suitable for use as co-stabilisers include monocyclic or polycyclic ethers which can optionally contain other hetero-atoms and which contain one or more substituted or unsubstituted, saturated or unsaturated rings containing 5 or 6 carbon atoms, such as 1,3-dioxane, 1,4-dioxane, 1,3,5-trioxane, 1,3-dioxolane, dioxene, dioxadiene, thioxane, oxazole, tetrahydrofuran, diphenyl ether and the like.

Ketones which can be used are substituted or unsubstituted ketones containing from 3 to 7 carbon atoms, such as, for example, acetone, methyl ethyl ketone, diethyl ketone, methyl propyl ketone, methyl isopropyl ketone, 1-(furan-2-yl)-propanone, 3-hydroxyhexane-2,5-dione, 2-methyl-2-hydroxypentan-4-one and the like.

Amines which are most frequently used are substituted or unsubstituted compounds containing from 3 to 10 carbon atoms, such as secondary and tertiary aliphatic amines and also aromatic amines, such as aniline, optionally substituted by $C_1$ to $C_4$ alkyl groups or chlorine atoms. The preferred aliphatic amines are triethylamine, diisopropylamine, amylamine and hexylamine. Other amines which can be used are heterocyclic compounds containing a nitrogen atom in the ring. Amongst these, those compounds containing from 4 to 12 carbon atoms and 1 to 2 nitrogen atoms in the molecule are normally used, such as pyridine, picolines, phenothiazine, morpholine and pyrrolidine and also their derivatives substituted by alkyl groups on the nitrogen atom. Finally, the very particularly preferred amines are N-methylmorpholine, diisopropylamine, pyrrolidone and N-methylpyrrole.

The phenolic compounds which are normally used can contain one or more hydroxyl groups bonded to a benzene nucleus which is optionally already substituted by alkyl groups. The preferred compounds are phenol and its alkylated derivatives such as thymol, cresols, para-methoxyphenol, methyl-di-tert.-butylphenols and dimethyl-tert.-butylphenols. Phenol, thymol and p-methoxyphenol are very particularly preferred.

Finally, the olefinic compounds which can be used as co-stabilisers are generally compounds containing one or more double bonds in the molecule and containing from 4 to 10 carbon atoms. Amongst these, the preferred compounds are tertiary amylene and diisobutylene.

Other compounds, in particular alkoxyalkanes such as alkoxyethanes, nitrates such as alkyl nitrates containing from 1 to 5 carbon atoms, quinones such as hydroquinone and anthraquinones, hydrazines such as dimethylhydrazine, and aromatic compounds such as toluene, can also be used as co-stabilisers.

These various co-stabilisers used are generally present in very variable amounts of between 0.001 and 50 g/liter of chlorinated solvent.

The compositions of chlorinated solvents stabilised according to the invention are particularly suitable for applications which simultaneously require a good stabilisation of the chlorinated solvent in question and the lowest possible total amount of stabilisers present. They are advantageously used hot, cold or in the vapour phase, for degreasing metals and very particularly for the degreasing of metals in the cold, since the compositions of chlorinated solvents stabilised according to the invention exhibit the characteristic of wetting metal parts very effectively.

The following may be mentioned as examples of compositions of chlorinated solvents stabilised according to the invention:

1,1,1-trichloroethane, an oxaziridine such as 2-tert.-butyloxaziridine, a nitroalkane such as nitromethane or nitroethane, a saturated aliphatic alcohol such as butyl alcohol or tertiary amyl alcohol, and an unsaturated aliphatic alcohol such as 2-methylbut-3-yn-2-ol;

trichloroethylene, an oxaziridine such as 2-tert.-butyloxaziridine, one or more amines, an ester such as ethyl acetate, and one or more phenols;

perchloroethylene, an oxaziridine such as 2-tert.-butyloxaziridine or 2-tert.-amyloxaziridine, one or more phenolic compounds, one or more epoxides and one or more amines; and methylene chloride, an oxaziridine such as 2-propyloxaziridine or 2-tert.-butyloxaziridine, one or more epoxides, one or more amines, an ester, nitromethane, an internal ether containing one or two oxygen atoms, and, if appropriate, an olefinic compound.

EXAMPLE 1

This example is provided by way of comparison

Experiment 1

100 cm³ of 1,1,1-trichloroethane, stabilised by 40 g/liter of tertiary butyl alcohol, 17.5 g/liter of 2-methylbut-3-yn-2-ol, 10 g/liter of nitromethane, 5.7 g/liter of epoxybutane and 100 cm³ of toluene, are introduced into a 500 cm³ round-bottomed flask equipped with a thermometer and fitted with a CLAISEN head, intended for suppressing exothermic decomposition reactions, which is surmounted by a reflux condenser equipped with a drying tube packed with grains of anhydrous $CaCl_2$. 18 g of aluminium turnings and 0.7 g of $AlCl_3$ are added to this mixture.

This mixture is boiled under reflux for 18 hours, with a break overnight, and no decomposition is observed.

Experiment 2

Experiment 1 is repeated, but 1,1,1-trichloroethane stabilised by 20 g/liter of tertiary butyl alcohol, 8.75 g/liter of 2-methylbut-3-yn-2-ol, 5 g/liter of nitromethane and 5.7 g/liter of epoxybutane is used.

This mixture is also boiled under reflux and undergoes exothermic decomposition after 12 hours.

EXAMPLE 2

Experiment 1

1,1,1-Trichloroethane stabilised by 20 g/liter of tertiary butyl alcohol, 8.75 g/liter of 2-methylbut-3-yn-2-ol, 5 g/liter of nitromethane and 8.0 g/liter of 2-tert.-butyloxaziridine is used under the same conditions as described for Example 1, Experiment 1.

After boiling under reflux for 18 hours, with a break overnight, no decomposition is observed.

Experiment 2

Experiment 1 is repeated, but a stabilisation formulation only containing 5.6 g/liter of 2-tert.-butyloxaziridine is used, and it is again found that there is no decomposition of the 1,1,1-trichloroethane under the above-mentioned conditions.

From a comparison of the results of Examples 1 and 2, it can be deduced that the use of an oxaziridine in a customary stabilisation formulation, instead of the epoxidised compound, makes it possible to reduce, by at least half, the amount of the other stabilisers required for obtaining a good stability.

We claim:

1. A stabilized composition containing a chlorinated solvent, which is stabilized by means of a heterocyclic compound containing an oxaziridine ring.

2. Composition according to claim 1, wherein the heterocyclic compound corresponds to the general formula

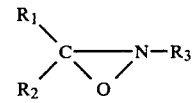

in which $R_1$, $R_2$ and $R_3$ are different or identical, organic or inorganic radicals.

3. Composition according to claim 1 or 2, wherein $R_1$, $R_2$ and $R_3$ are chosen from amongst the hydrogen atom, alkyl radicals containing from 1 to 8 carbon atoms and aromatic radicals containing not more than 8 carbon atoms.

4. Composition according to either one of claims 1 or 2, wherein at least one of the radicals $R_1$, $R_2$ or $R_3$ is a branched alkyl radical.

5. Composition according to claim 4, wherein at least $R_3$ is a branched alkyl radical.

6. Composition according to claim 1, wherein the heterocyclic compound is 2-tert.-butyloxaziridine, 2-tert.-amyloxaziridine or 2-isopropyloxaziridine.

7. Composition according to claim 1, wherein the heterocyclic compound is present in an amount of 0.001 mol to 0.5 mol per liter of chlorinated solvent.

8. Composition according to claim 7, wherein the heterocyclic compound is present in an amount of 0.01 to 0.2 mol per liter of chlorinated solvent.

9. Composition according to claim 1, wherein the chlorinated solvent is 1,1,1-trichloroethane.

10. Composition according to claim 9, which contains, as a co-stabilizer, a saturated aliphatic alcohol, an unsaturated aliphatic alcohol and a nitroalkane.

11. Composition according to claim 2, wherein the heterocyclic compound in present in an amount of 0.001 mol to 0.5 mol per liter of chlorinated solvent.

12. Composition according to claim 3, wherein the heterocyclic compound in present in an amount of 0.001 mol to 0.5 mol per liter of chlorinated solvent.

13. Composition according to claim 4, wherein the heterocyclic compound in present in an amount of 0.001 mol to 0.5 mol per liter of chlorinated solvent.

14. Composition according to claim 2, wherein the chlorinated solvent is 1,1,1-trichloroethane.

15. Composition according to claim 14, wherein the heterocyclic compound is present in an amount of 0.001 mol to 0.5 mol per liter of chlorinated solvent.

16. Composition according to claim 15, wherein $R_1$, $R_2$ and $R_3$ are chosen from amongst the hydrogen atom, alkyl radicals containing from 1 to 8 carbon atoms and aromatic radicals containing not more than 8 carbon atoms.

17. Composition according to claim 15, which contains, as a co-stabilizer, a saturated aliphatic alcohol, an unsaturated aliphatic alcohol and a nitroalkane.

* * * * *